| United States Patent [19]
Fletcher et al.

[11] 3,975,436
[45] Aug. 17, 1976

[54] BENZYLAMINE NARCOTIC ANTAGONISTS

[75] Inventors: Horace Fletcher, Pottstown; Jerry L. Malis, Bluebell; John P. Yardley, King of Prussia, all of Pa.

[73] Assignee: American Home Products Corporation, New York, N.Y.

[22] Filed: Oct. 30, 1975

[21] Appl. No.: 627,485

Related U.S. Application Data

[62] Division of Ser. No. 455,172, March 27, 1974, Pat. No. 3,937,818.

[52] U.S. Cl.................... 260/570.5 R; 260/501.17; 260/600 R; 424/316; 424/330
[51] Int. Cl.²......................................... C07C 87/28

[58] Field of Search.............. 260/570.5 R, 570.8 R, 260/501.17

[56] References Cited
UNITED STATES PATENTS
2,133,779  10/1938  Clifford..................... 260/570.6 X Primary Examiner—Robert V. Hines
Attorney, Agent, or Firm—Robert Wiser

[57] ABSTRACT

A process for antagonizing the pharmacologic effects of a narcotic agent in warm-blooded animals, and compositions for effecting this process are disclosed.

2 Claims, No Drawings

BENZYLAMINE NARCOTIC ANTAGONISTS

This is a division of application Ser. No. 455,172, filed Mar. 27, 1974, now U.S. Pat. No. 3,937,818.

BACKGROUND OF THE INVENTION

The problems associated with narcotic abuse and addiction and of the seemingly ubiquitous narcotics addict are very well known in today's society. Also well-known are the problems associated with curing an addict of his drug dependence. Because very often there is a psychological as well as a physiological dependence, the addict, once he has been withdrawn (cured) from his physiological drug dependence will often return to narcotic usage for other, possibly psychological, reasons. Thus a long term treatment and rehabilitation program for the narcotics addict has been suggested as being necessary (p. 259. A. Goth. Medical Pharmacology, 2nd. ed., C. V. Mosby, 1964). In addition, this long term program should allow the addict to otherwise function normally (i.e. attend school, maintain a job) during the ameliorative process. The drug, methadone, is today being utilized to aid in such long term treatment and rehabilitation programs.

A major problem associated with long term methadone therapy is the fact that the drug itself is an addicting narcotic with euphoriant properties; thus one is not curing addiction but merely making it less objectionable.

It is well-known (see for example, pp. 274–278, The Pharmacological Basis of Therapeutics, L. S. Goodman, and A. Gillman, Third ed., 1966, MacMillan), that certain agents (called narcotic antagonists) are able to prevent or abolish some or all of the clinical effects of a dose of morphine or heroin in man and animals. Thus, for example, nalorphine prevents or abolishes, in appropriate species, narcotic induced euphoria, analgesia, drowsiness, respiratory depression and other well-known effects and side effects associated with narcotic usage. Several narcotic antagonists are in use clinically, for example, to treat narcoticinduced respiratory depression. It is also known that in patients who are physically dependent on narcotic usage small doses of a narcotic antagonist, such as nalorphine, will precipitate acute withdrawal symptoms qualitatively identical to those seen after abrupt withdrawal of the narcotic agent. Thus, administration of the antagonist may be used as a simple, albeit unpleasant, method to test for physical dependence of the suspected narcotics addict.

Many reports in the recent literature (see for example, Agonist and Antagonist Actions of Narcotic Analgesic Drugs, H. W. Kosterlitz, H. O. J. Collier, and J. E. Fillarreal, editors, MacMillan, 1972, and references cited therein) propose the prophylactic use of a narcotic antagonist as an alternate medicinal approach to methadone therapy for the long term treatment and amelioration of narcotics addicts. Thus, it has been observed (M. Fink, A. M. Freedman, P. Resmick and A. Zaks in Agonist and Antagonist Actions of Narcotic Analgesic Drugs, H. W. Kosterlitz, H. O. J. Collier, and J. E. Villarreal, editors, MacMillan, 1972) that when most previously detoxified narcotics addicts, who are receiving prophylactic therapy with a narcotic antagonist, are challenged with a narcotic agent they do not experience any of the expected clinical effects of the narcotic and their use of narcotic agents, in most cases, is eventually reduced.

SUMMARY OF THE INVENTION

The invention sought to be patented in its process aspect resides in the concept of a process for antagonizing the effect of a narcotic agent in warm-blooded animals which comprises administering to a warm-blooded animal in need thereof a sufficient amount of a compound of the formula:

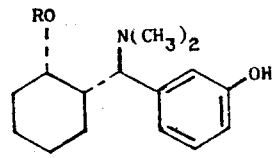

wherein R is ethyl or benzyl; and the pharmacologically acceptable acid addition salts thereof.

The invention sought to be patented in its first subgeneric process aspect resides in the concept of the process for antagonizing the effect of a narcotic agent in warm-blooded animals which comprises administering to a warm-blooded animal in need thereof a sufficient amount of the compound α-dimethylamino-α-(cis-2-ethoxy-cyclohexyl)-m-cresol.

The invention sought to be patented in its second subgeneric process aspect resides in the concept of the process for antagonizing the effect of a narcotic agent in warm-blooded animals which comprises administering to a warm-blooded animal in need thereof a sufficient amount of the compound α-dimethylamino-α-(cis-2-benzyloxycyclohexyl)-m-cresol.

The invention sought to be patented in its third subgeneric process aspect resides in the concept of the process for antagonizing the effect of a narcotic agent in warm-blooded animals which comprises administering to a warm-blooded animal in need thereof a sufficient amount of the compound (1)-α-dimethylamino-2-(cis-2-benzyloxycyclohexyl)-m-cresol.

The invention sought to be patented in a principal composition aspect resides in the concept of the compound having the formula:

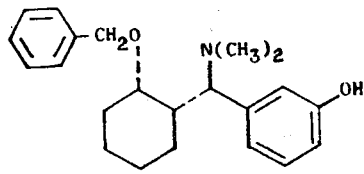

substantially free of the trans epimer; and the pharmacologically acceptable acid addition salts thereof.

The tangible embodiments of the principal composition aspect of the invention possess the inherent general physical properties in the free base form of being colorless to yellow oils, or solids, substantially insoluble in water, and generally soluble in organic solvents such as ether, benzene, hexane, acetone and pyridine. In the form of their acid addition salts they are generally white or off-white crystalline solids, appreciably soluble in water. Examination of the compound reveals, upon infrared, ultraviolet, and nuclear magnetic resonance spectrographic analysis, spectral data supporting the molecular structure hereinbefore set forth. The aforementioned physical characteristics, taken together with the nature of the starting materials, the elemental analysis, and the products obtained therefrom, further confirm the molecular structure hereinbefore set forth.

The tangible embodiments of the principal composition aspect of the invention possess the inherent applied use characteristic of exerting narcotic antagonizing effects in warm-blooded animals as evidenced by pharmacological evaluation according to standard test procedures. In addition, the dose needed to produce these desirable narcotic antagonizing effects has been demonstrated to elicit, at most, only minimal analgesic effects when evaluated by standard pharmacological test procedures.

The invention sought to be patented in a second composition aspect resides in the concept of a composition suitable for administration to a warm-blooded animal comprising:

a. the compound of the formula:

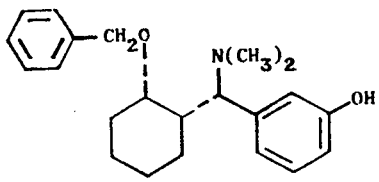

and the pharmacologically acceptable acid addition salts thereof;
and b. a pharmacologically acceptable carrier.

DESCRIPTION OF THE PREFERRED EMBODIMENTS

A convenient starting material for preparing the compositions of the instant invention is dl-cis-2-($\alpha$-dimethylamino-m-methoxymethoxybenzyl)cyclohexanol. This material may be prepared, for example, by condensing m-methoxymethoxybenzaldehyde and cyclohexanone under basic conditions to produce m-methoxymethoxybenzalcyclohexanone, which is reacted with dimethylamine producing dl-2-($\alpha$-dimethylamino-m-methoxymethoxybenzyl)cyclohexanone. Reduction of the ketone function produces a mixture of the cis and trans, dl-amino alcohols. The separation of the cis and trans isomers as well as the resolution of their respective racemic mixtures is within the skill of the art. This synthesis of starting material, as well as the isolation of the cis isomer, and the resolution of the dl racemic mixture, is fully described in the art, for example in Belgian Pat. No. 797,827. The remainder of the synthesis of the compositions of the invention will now be described using as an example, the specific product, 1-$\alpha$-dimethylamino-$\alpha$-(cis-2-benzyloxycyclohexyl)-m-cresol.

The secondary alcohol function of 1-cis-2-($\alpha$-dimethylamino-m-methoxymethoxybenzyl)cyclohexanol is first metalated, for example, by treatment with n-butyl lithium in tetrahydrofuran. The resulting lithium alcoholate is next alkylated with benzyl chloride and after acid hydrolysis of the methoxymethoxyl protecting group, the product, 1-$\alpha$-dimethylamino-$\alpha$-(cis-2-benzyloxycyclohexyl)-m-cresol is isolated and may be purified by standard procedures, for example, column chromatography and recrystallization. It will be obvious to those skilled in the art that treatment of the lithium alcoholate of 1-cis-2-($\alpha$-dimethylamino-m-methoxymethoxybenzyl) cyclohexanol with an ethylating agent such as triethyloxonium fluoroborate will enable one to prepare 1-$\alpha$-dimethylamino-$\alpha$-(cis-2-ethoxycyclohexyl)-m-cresol by a process analogous to that outlined above.

It will be obvious to those skilled in the art that the 1-cis isomer of the amino alcohol will yield 1-cis products and that utilization of d-cis or dl-cis amino alcohols will likewise yield d-cis or dl-cis products, and that the utilization of these additional isomers in the above described reactions is fully equivalent to and contemplated by the teachings herein.

In practicing the process aspect of the invention, the instant compositions can be administered in a variety of dosage forms, the oral route being used primarily for maintenance therapy while injectables tend to be more useful in acute emergency situations.

The daily dose requirements vary with the particular compositions being employed, the severity of the symptoms being presented, and the animal being treated.

The dosage also varies with the size of the animal. With large animals (about 70 kg. body weight), by the oral route, the dose is from about 5 milligrams to about 100 milligrams, and preferably from about 10 to 50 milligrams, approximately every 4 hours, or as needed. By parenteral route, the ordinarily effective dose is from about 20 milligrams to about 50 milligrams, preferably about 25 milligrams per day.

For unit dosages, the active ingredient can be compounded into any of the usual oral or parenteral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. For compounding parenteral dosage forms the active ingredient can be suspended in various isotonic media such as glucose or saline solution or the active ingredient in the form of an acid addition salt may be dissolved in an isotonic medium and injected as a solution. In all cases, of course, the proportion of the active ingredient in said composition will be sufficient to impart narcotic antagonizing activity thereto. This will range upward from about 0.0001 percent by weight of active ingredient in said composition.

As has been previously stated, the dose necessary to evoke narcotic antagonism in warm-blooded animals has been observed to produce only minimal analgesic effects when tested in the same species of animal. This broad separation of narcotic antagonizing and analgesic effects is a desirable characteristic and is an additional benefit inuring to the practice of the instant invention. Thus, for example, a withdrawn narcotics addict receiving prophylactic therapy with a narcotic antagonist as taught by the instant invention would not be expected to experience any significant analgesia, ordinarily considered an undesirable unnecessary and unwanted side effect of narcotic antagonist maintanance therapy.

Where used in this specification and claims, the terminology "antagonizing the effect of a narcotic agent" means:

1. the reversal of the clinical manifestations of a narcotic overdose, such as respiratory depression; and 2. the elimination of the euphoriant and other effects of narcotic usage which are sought after by one who abuses narcotic drugs.

The following examples further illustrate the best mode contemplated by the inventors of carrying out their invention.

EXAMPLE 1 m-Methoxymethoxybenzalcyclohexanone m-Methoxymethoxybenzaldehyde (167 g., 1.0 mole) and cyclohexanone (318 ml., 3.0 moles) were refluxed for 4 hours under nitrogen with a solution of potassium hydroxide (50 g., 0.89 moles) in water (1 liter). After cooling the oily layer was extracted with ether (twice). The ether solution was washed with water (thrice), brine, dried ($Na_2SO_4$), and evaporated. The residue was distilled and the product obtained as a yellow oil (132 g.), b.p. 173°–176° at 0.3 mm. $\lambda_{max}^{95\% \, EtOH}$ 287 m$\mu$ ($\epsilon$ 13,100). I. R. Max $_{KBr}$ 1685, 1600, 1580 cm$^{-1}$. NMR ($CDCl_3$): $\delta$ 5.2 (2H singlet, -O$\underline{CH}_2$O), 3.48 (3H singlet, -O$\underline{CH}_3$).

EXAMPLE 2

Cis-2-[α-Dimethylamino-m-(Methoxymethoxy)Benzyl]Cyclohexanol and Trans-2-[α-Dimethylamino-m-(Methoxymethoxy)Benzyl] Cyclohexanol Maleate A solution of m- methoxymethoxybenzalcyclohexanone (100 g. 4 × 10$^{-1}$ moles) in ether (100 ml.) was cooled to −5° in a pressure bottle and treated with 50 ml. dimethylamine (7.5 × 10$^{-1}$ moles) and left at room temperature during 60 hours. The reaction mixture was then added dropwise under nitrogen to a stirred suspension of $LiAlH_4$ (20 g.) in ether (1.4 liters) over 1 hour. The reaction mixture was stirred during one further hour and then refluxed during 2 hours. The ice cooled reaction mixture was treated with 3% aqueous NaOH solution (100 ml.) and filtered. The precipitated solids were washed with boiling ether and the combined filtrates evaporated to a volume of about 1 liter. The ether layer was extracted (twice) with an excess of dilute HCl followed by a water extraction. The combined aqueous extracts were back washed with ether basified with ice and 50% NaOH and extracted with ether (twice). The ether layers were washed with brine, dried ($K_2CO_3$) and evaporated to an oil (46 g.) shown by glc to consist of two major components. The oil was chromatographed on a Woelm alumina column (1.5 Kg. neutral activity Grade III) built in benzene-hexane 1:1. Benzenehexane, benzene and early benzene 10% ether fractions eluted 25.8 g. trans-2-[α-dimethylamino-m-methoxymethoxy)benzyl]cyclohexanol. NMR ($CDCl_3$): $\delta$ 2.28 (6H singlet, N(C$\underline{H}_3$)$_2$), 3.0 (1H doublet J=3 cps, C$\underline{H}$ N(CH$_3$)$_2$), 3.3–3.8 (1H broad multiplet CH OH), 3.48 (3H singlet, OCH$_3$), 5.17 (2H singlet, —OC$\underline{H}_2$O—) ppm.

Later benzene-ether fractions (9:1 through 1:2) eluted cis-2-[α-dimethylamino-m-(methoxymethoxy)-benzyl]cyclohexanol.

NMR ($CDCl_3$): $\delta$ 2.1 (6H singlet, N(C$\underline{H}_3$)$_2$), 3.47 (3H singlet, —OCH$_3$), 3.37–3.7 (overlapping multiplets C$\underline{H}$ OH and C$\underline{H}$ N(CH$_3$)$_2$), 5.21 (2H singlet —OC$\underline{H}_2$O—) ppm.

The maleate salt of the trans compound, m.p. 147°–148°, was crystallized from acetone-dichloromethane. NMR ($CDCl_3$): $\delta$ 2.97 (6H singlet, N(CH$_3$)$_2$), 3.48 (3H singlet, -OCH$_3$), 3.73 (1H broad multiplet, CH OH), 4.0 (1H singlet, J=3 cps CH N(CH$_3$)$_2$), 5.2 (2H singlet, —OCH$_2$O—), 6.3 (2H singlet, vinylic proton maleate anion), 10.75 (3H broad peak W ½ H 24 cps - exchangeable protons). Found: C, 61.74; H, 7.77; N, 3.19. Calcd. for $C_{21}H_{31}NO_7$ (409.47): C, 61.59; H, 7.63; N, 3.42.

EXAMPLE 3 dl-α-Dimethylamino-α-(cis-2-Ethoxycyclohexyl)-m-Cresol, Hydrochloride, Hemihydrate The lithium alcoholate of dl-cis-2-(α-dimethylamino-m-methoxymethoxybenzyl)cyclohexanol [prepared from 11.8 g., (.04 mol.) of amino alcohol and 25 ml. of 1.6M butyl lithium in tetrahydrofuran] was stirred, under nitrogen, overnight with triethyloxonium fluoroborate [prepared from .045 mol. epichlorohydrin as described by Meerwein, Org. Syn. 46, 113 (1966).

The reaction mixture was filtered from solids and evaporated to an oil. The oil was dissolved in ether, washed with 1N NaOH and extracted with cold 1N $H_2SO_4$. The aqueous layer was washed with ether, made basic with 4N NaOH, and re-extracted into ether. The ether extract was washed with water and dried ($Na_2SO_4$).

Tlc analysis indicated a mixture of starting material and a less polar product which were separated by descending column chromatography on a Woelm alumina column developed with chloroform. The less polar fraction (4 g.) of cis-2-ethoxy-α-(m-methoxymethoxyphenyl)-N,N-dimethylcyclohexanemethylamine was obtained as an oil. NMR ($CDCl_3$): $\delta$ 2.1 (6H singlet N(CH$_3$)$_2$), 1.04 (3H triplet J=7 cps., C$\underline{H}_3$CH$_2$O-), 3.47 (3H singlet C$\underline{H}_3$OCH$_2$O-), 5.15 (2H singlet CH$_3$OC$\underline{H}_2$O-) ppm. The oil in tetrahydrofuran (100 ml.) was treated with 5 ml. 4.6H isopropanolic HCl during 4 days at room temperature. Evaporation afforded dl-α-dimethylamino-α-(cis-2-ethoxycyclohexyl)-m-cresol, hydrochloride, hemihydrate as a hygroscopic solid, m.p. 155°–160°. Found: C, 63.09; H, 9.26; N, 4.37. $C_{17}H_{27}NO_2 \cdot HCl \cdot \frac{1}{2} H_2O$ requires: C, 63.23; H, 9.05; N, 4.34%.

EXAMPLE 4

α-Dimethylamino-α-(cis-2-Benzyloxycyclohexyl)-m-Cresol, Hydrochloride l-isomer 1-Cis-2-(α-dimethylamino-m-methoxymethoxybenzyl)cyclohexanol (10 g., 34 mmol.) in dry tetrahydrofuran was treated with a solution of n-butyl lithium in hexane (1.6 molar, 24.5 ml., 39 mmol.) at 0°. After 45 min. the reaction mixture was cooled to −70° and treated with a solution of benzyl chloride (4.3 g., 3.9 ml., 34 mmol.) in tetrahydrofuran (20 ml.) followed by sodium iodide 5.1 g. (34 mmol.). The reaction mixture was refluxed, under nitrogen during 24 hr., filtered from solids and evaporated to an oil. The oil was dissolved in ether, washed with 1N NaOH and extracted with cold 1N $H_2SO_4$. The aqueous layer was washed with ether, made basic with 4N NaOH, and re-extracted into ether. The ether extract was washed with water and dried ($Na_2SO_4$). Tlc indicated a mixture of approximately equal quantities of a less polar product with starting material. The residue (10.5 g.) after evaporation of the ether was subjected to descending dry-column chromatography on Woelm alumina. Elution with chloroform afforded 5.0 g. of oily 1-cis-benzyloxy-α-(m-methoxymethoxyphenyl)-N,N-dimethylcyclohexane methylamine [α]$_D$ −118.9° (c, 0.979 methanol). NMR (CDCl$_3$): δ 2.12 (6H singlet N(C$\underline{H}$$_3$)$_2$—), 3.45 (3H singlet, C$\underline{H}$$_3$O—CH$_2$—), 5.17 (2H singlet CH$_3$OC$\underline{H}$$_2$—), 7.39 (5H singlet, C$_6$$\underline{H}$$_5$CH$_2$O). Further elution of the column with CHCl$_3$:MeOH (3:1) afforded 5 g. of starting material. The 1-cis-benzyloxy-α-(m-methoxymethoxyphenyl)-N,N-dimethylcyclohexane methylamine (4.5 g.) in tetrahydrofuran (50 ml.) was treated with 5 ml. of 4.6N HCl in isopropanol at room temperature during 60 hours. After evaporation of solvent the residue was triturated with ether and recrystallized from acetone to give 1-α-dimethylamino-α-(cis-2-benzyloxycyclohexyl)-m-cresol, hydrochloride, hemiacetone solvate, m.p. 175°–176°, [α]$_D$ −83.15° (c, 0.989 methanol) NMR: (DMSO) δ 2.08 (3H singlet ½ C$\underline{H}$$_3$COC$\underline{H}$$_3$). Found: C, 69.41; H, 8.43; N, 3.38; Cl, 9.21. C$_{22}$H$_{30}$NO$_2$Cl.½ CH$_3$COCH$_3$ requires: C, 69.68; H, 8.21; H, 3.46; Cl, N, 8.75%. dl-series In a similar manner there was obtained dl-α-dimethylamino-α(cis-2-benzyloxycyclohexyl)-m-cresol, hydrochloride m.p. 257°–258°. Found: C, 70.27; H, 8.18; N, 3.45; Cl, 9.64. C$_{22}$H$_{30}$NO$_2$Cl requires: C, 70.29; H, 8.04; N, 3.73; Cl, 9.43%.

EXAMPLE 5

Antagonism of Morphine Induced Loss of Righting Reflex

Groups of three male Charles River rats (160 to 200 g.) were dosed subcutaneously with morphine base at 75 mg/kg. The degree of narcosis was measured at 15 and 30 minutes after injection. Criterion was loss of righting reflex. Antagonists were administered 40 minutes after the morphine. The degree of antagonism was measured at 20 minute intervals for 2 hours. Nalorphine at 2 mg/kg. served as a positive control while one group of morphinized rats in each determination received no antagonist and served as negative controls. Compounds were dissolved in water or suspended in Tween-80 and water and were administered intramuscularly. Each dose of the antagonist was tested in a minimum of three experiments. At least three doses of each antagonist was used to determine the ED$_{50}$. For each experiment the degree of reversal, by the antagonist, of the loss of righting reflex induced by morphine was calculated in the following manner. The total number of periods of loss of righting reflex in the experimental group was divided by the total number of periods of loss of righting reflex in the control group. This number was converted to percent and subtracted from 100 to give percent reversal of loss of righting reflex. The dose for which a 50% reversal of the loss of righting reflex was observed is the ED$_{50}$.

Results

| Compound | ED$_{50}$ (Mg/kg) |
|---|---|
| (dl)-α-dimethylamino-α-(cis-2-ethoxycyclohexyl)-m-cresol | 2.0 |
| (dl)-α-dimethylamino-α-(cis-2-benzyloxycyclohexyl)-m-cresol | 0.95 |
| (l)-α-dimethylamino-α-(cis-2-benzyloxycyclohexyl)-m-cresol | 0.35 |
| Nalorphine | 1.0 |

The subject matter which the applicants regard as their invention is particularly pointed out and distinctly claimed as follows:

1. The compound having the formula:

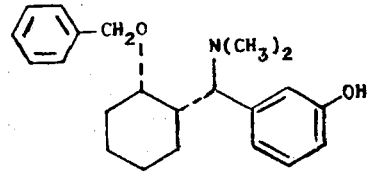

substantially free of the trans epimer; and the pharmacologically acceptable acid addition salts thereof.

2. The compound according to claim 1 substantially free from its d-enantiomer; and the pharmacologically acceptable acid addition salts thereof.

* * * * *